(12) United States Patent
Correia et al.

(10) Patent No.: US 11,465,964 B2
(45) Date of Patent: Oct. 11, 2022

(54) PROCESS FOR THE PREPARATION OF METFORMIN

(71) Applicant: Merck Patent GmbH, Darmstadt (DE)

(72) Inventors: Camille Correia, Heppenheim (DE); Renaud Poli, Nimes (FR); Serge Gerbaut, Jonage (FR); Marc Dittmann, Pfungstadt (DE); David Maillard, Darmstadt (DE); Sebastian Haertner, Muehltal (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/967,781

(22) PCT Filed: Feb. 5, 2019

(86) PCT No.: PCT/EP2019/052689
§ 371 (c)(1),
(2) Date: Aug. 6, 2020

(87) PCT Pub. No.: WO2019/154769
PCT Pub. Date: Aug. 15, 2019

(65) Prior Publication Data
US 2021/0040035 A1    Feb. 11, 2021

(30) Foreign Application Priority Data
Feb. 7, 2018 (EP) .................... 18155451

(51) Int. Cl.
*C07C 277/08* (2006.01)
*C07C 279/26* (2006.01)

(52) U.S. Cl.
CPC .......... *C07C 277/08* (2013.01); *C07C 279/26* (2013.01); *C07B 2200/13* (2013.01)

(58) Field of Classification Search
None
See application file for complete search history.

(56) References Cited

U.S. PATENT DOCUMENTS

| 2002/0172722 A1* | 11/2002 | Fanelli | A61K 33/26 424/647 |
| 2013/0225846 A1* | 8/2013 | Domaille | C12M 47/10 554/206 |
| 2014/0296496 A1* | 10/2014 | Zhang | A61P 37/04 536/3 |

FOREIGN PATENT DOCUMENTS

| CN | 105481726 A | 4/2016 |
| IN | 201621016063 A | 11/2017 |

OTHER PUBLICATIONS

Tongtao et al., "Synthesis of Developer Metfomine Hydrochloride", Chemical Industry Times, 2010, 24(9), 17-19 (with English abstract).
International search report PCT/EP2019/052689 dated May 3, 2019 (pp. 1-3).

* cited by examiner

*Primary Examiner* — Sudhakar Katakam
*Assistant Examiner* — Jennifer C Sawyer
(74) *Attorney, Agent, or Firm* — Millen, White, Zelano and Branigan, P.C.; Harry B. Shubin

(57) ABSTRACT

The present invention relates to an improved process for the preparation of metformin hydrochloride, an important drug in the first line treatment of Type II Diabetes.

13 Claims, No Drawings

PROCESS FOR THE PREPARATION OF METFORMIN

The present invention relates to an improved process for the preparation of metformin hydrochloride, an important drug in the first line treatment of Type II Diabetes.

Metformin can be prepared via the condensation of dimethylammonium chloride and dicyanodiamide as depicted below:

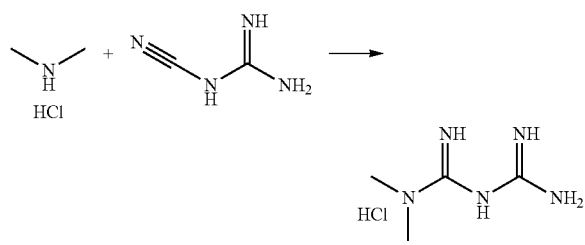

Typically, the reaction is commonly carried out at a high temperature in hydrocarbon or alcoholic solvents.

Examples of prior art wherein a hydrocarbon, such as xylenes, is chosen as the solvent, are disclosed in DE 1023757, Indian Patent Application No. 1350/MUM/2007, Indian Patent Application No. 1346/MUM/2008 and FR Patent Application No. 2322860.

Examples of prior art wherein alcoholic solvents were chosen are CN 105481726 A, CN 100391939 C and CN 106795104 A.

Anvar Shalmashi (Molbank, 2008, M564) disclosed a synthetic route to metformin hydrochloride by microwave irradiation on thin layer chromatography (TLC) plates.

All methods described in the prior art must take into consideration the removal of the solvent to ensure purity of the final product, as well as safety concerns regarding protection against flammable organic solvents. Further, residual amounts of solvents in the final product cannot entirely be excluded, which is critical from the toxicological point of view. In principle, the reaction in the absence of organic solvent is desirable and would be a preferred and safer alternative.

A synthesis of metformin hydrochloride in the absence of a solvent is disclosed in Indian Patent Application Number 189077. According to such teaching dicyanodiamide and dimethylammonium chloride (the reactants) are mixed together with wet metformin hydrochloride (the product) in a ratio of from 1:1 to 1.3:1-3 and reacted at temperatures below 150° C. To obtain sufficient conversions of the reactants to the product, metformin hydrochloride has to be added to the reaction mixture in an equimolar or excess amount.

Addition of metformin hydrochloride to the reactants in at least equimolar amounts requires bigger reactor sizes and increased energy input and reduces the output of the reaction product compared to the reactants (only a part of the metformin hydrochloride in the product is newly synthesized). Further, metformin HCl fed to the reaction may undergo degradation when the reaction mixture is heated thereby leading to an increased content of impurities in the final product that has to be removed from the reaction product after the reaction. In addition to further increased costs, the entire time span of the reaction is significantly increased.

Therefore, it was an object of the present invention to provide a process for the preparation of metformin that is not afflicted with the above-mentioned disadvantages of the existing production processes. Especially, the process should avoid the use of organic solvents and should not require the addition of metformin HCl in at least equimolar amounts.

These objects have been achieved by a process for the production of metformin HCl that comprises the following steps: (a) heating a mixture of dimethylammonium chloride, dicyanodiamide, water in an amount from 0 to 20% by weight and metformin HCl in an amount from 0 to 50% by weight, each based on the total weight of dimethylammonium chloride and dicyanodiamide present in the mixture, to a temperature in the range from 70° C. to 250° C. and maintaining the temperature in such range for a time from 0.1 minutes to 20 hours; (b) cooling the reacted mixture and collecting crystalline metformin HCl obtained.

The invention therefore related to a process for the production of metformin HCl that comprises the following steps: (a) heating a mixture of dimethylammonium chloride, dicyanodiamide, water in an amount from 0 to 20% by weight and metformin HCl in an amount from 0 to 50% by weight, each based on the total weight of dimethylammonium chloride and dicyanodiamide present in the mixture, to a temperature in the range from 70° C. to 250° C. and maintaining the temperature in such range for a time from 0.1 minutes to 20 hours; (b) cooling the reacted mixture and collecting crystalline metformin HCl obtained.

Due to the exothermic nature of the reaction and crystallization, a slower increase in temperature allows better control of the heat dissipated in a batch reactor.

Preferably, all reaction steps are conducted under stirring, preferably under constant stirring.

The process described above is a batch process. The term "batch process" as used herein refers to a process in which the raw materials are combined in a reactor or vessel and the product is removed at the end of the reaction.

Alternatively, the process can be also run as a continuous process. The term "continuous process" as used herein refers to a process in which there is a continuous inflow of raw materials and outflow of product. Such continuous processing enables a platform where the final product may be synthesized by a fully continuous train of operations starting from initial starting materials. In some examples, the production of the final product may be synthesized using a combination of batch and flow processing.

Running the process as continuous process is advantageous as it offers a safe, rapid and scalable path to increase productivity and to meet future demand for metformin hydrochloride. Such process for the preparation of metformin HCl comprises the steps (a) continuously feeding dimethylammonium chloride, dicyanodiamide, water in an amount from 0 to 20% by weight and metformin HCl in an amount from 0 to 50% by weight, each based on the total weight of dimethylammonium chloride and dicyanodiamide present in the mixture to a reactor under continuous stirring and under continuous heating the mixture to a temperature in the range from 70° C. to 250° C.; and (b) cooling the reacted mixture and collecting crystalline metformin HCl obtained. Accordingly, the present invention is also directed to a process for the preparation of metformin HCl comprising the steps (a) continuously feeding dimethylammonium chloride, dicyanodiamide, water in an amount from 0 to 20% by weight and metformin HCl in an amount from 0 to 50% by weight, each based on the total weight of dimethylammonium chloride and dicyanodiamide present in the mixture, to a reactor under continuous stirring and under continuous heating the mixture to a temperature in the range from 70° C. to 250° C.; and (b) cooling the reacted mixture and collecting crystalline metformin HCl obtained.

In an advantageous embodiment of the process of the present invention, in the batch process as well in the continuous process, metformin HCl can be present in an amount from 0 to 20% by weight, preferably in an amount from 0 to 10% by weight, more preferably in an amount of about 5% by weight and most preferably in an amount of 0% by weight, each based on the total weight of dimethylammonium chloride and dicyanodiamide present in the mixture. Accordingly, the present invention is also directed to the process which is characterized in that metformin HCl is present in an amount from 0 to 20% by weight, preferably in an amount from 0 to 10% by weight, more preferably in an amount of about 5% by weight and most preferably in an amount of 0% by weight, each based on the total weight of dimethylammonium chloride and dicyanodiamide present in the mixture.

In step (a) of the continuous or batch process the mixture can be heated to one, two or more different temperatures in a stepwise manner, i.e. in one, two, or more stages. In an advantageous embodiment the mixture is heated in step (a) in two stages, whereby the mixture is heated to a first temperature in the range from 70° C. to 120° C., which is maintained for a certain time, and then heated to a second temperature in the range from 120° C. to 250° C., which temperature is maintained for a certain time. Accordingly, the invention is also directed to a process, which is characterized in that in step (a) the mixture is heated to a first temperature in the range from 70° C. to 120° C., which is maintained for a certain time, and then heated to a second temperature in the range from 120° C. to 250° C., which temperature is maintained for a certain time.

The continuous process can be run in one continuous reactor or in a combination of continuous reactors in series. Therefore, the present invention is further directed to the process, that is characterized in that it is run in one continuous reactor or in a combination of continuous reactors in series.

According to an advantageous embodiment of the continuous process the mixture is heated in a first reactor to a first temperature in the range from 70° C. to 120° C., which temperature is maintained for a certain time, then heated in a second reactor in the range from 110° C. to 160° C., which temperature is maintained for a certain time and then heated in a third reactor to a third temperature in the range from 140° C. to 250° C., which temperature is maintained for a certain time. Thus, the invention is also directed to a continuous process for the preparation for metformin HCl that is characterized in that in step (a) the mixture is heated in a first reactor to a first temperature in the range from 70° C. to 120° C., which temperature is maintained for a certain time, then heated in a second reactor to a second temperature in the range from 110° C. to 160° C., which temperature is maintained for a certain time and then heated in a third reactor to a third temperature in the range from 140° C. to 250° C. which temperature is maintained for a certain time. The temperature and residence time of each step is dependent on the type of reactor technology chosen.

Depending from the type and dimension of the equipment used for running the continuous or batch process, from the applied production parameters such as feeding rate of the raw materials and stirring rate and from the heating temperature, the time of heating that is necessary for melting and reacting of the raw materials to the product can vary over a wide range. When running the process under usual conditions the sum of all times at which the heating temperature(s) is/are maintained for a certain time ranges from 0.1 minutes to 10 hours. Accordingly, the invention is further directed to the process that is characterized in that the sum of all times at which the heating temperature(s) is/are maintained for a certain time ranges from 0.1 minutes to 10 hours.

In one example of the invention the process is a continuous process and run with three heating stages. In such example, it is advantageous if the heating temperatures are maintained from 0.1 min to 2 hours for the first temperature, from 0.1 min to 3 hours for the second heating temperature and 0.1 min to 5 hours for the third heating temperature. Accordingly, the present invention is also directed to a continuous process for the preparation of metformin, wherein the first heating temperature is maintained for 0.1 min to 2 hours, the second heating temperature is maintained for 0.1 min to 3 hours and the third heating temperature is maintained for 0.1 min to 5 hours.

In an especially preferred embodiment the process for the preparation of metformin HCl is characterized in that it comprises the steps (a) continuous feeding anhydrous dimethylammonium chloride, dicyanodiamide and water in an amount from 0 to 20% by weight based on the total weight of dimethylammonium chloride and dicyanodiamide present in the mixture to a continuous reactor and heating the mixture to a first heating temperature in the range from 70° C. to 120° C. which heating temperature is maintained for 0.1 to 2 hours, then increasing the temperature to a second temperature in the range from 110° C. to 160° C. and maintaining the temperature in such range for a time from 0.1 minutes and 3 hours and then increasing the temperature to a third temperature in the range from 140° C. to 250° C. and maintaining that temperature from 0.1 mins to 5 hours; (b) cooling the reacted mixture and collecting crystalline metformin HCl obtained.

As used herein, "about" refers to a numeric value, including, for example, whole numbers, fractions, and percentages, whether or not explicitly indicated. The term "about" generally refers to a range of numerical values (e.g., +/−1-3% of the recited value) that one of ordinary skill in the art would consider equivalent to the recited value (e.g., having the same function or result). In some instances, the term "about" may include numerical values that are rounded to the nearest significant figure.

Generally, if in the present application the term "process" is used without any further specification the respective disclosure is related to both, the batch process as well to the continuous process. If the term "process" is used together with the term "continuous", i.e. "continuous process", the respective disclosure is related to the continuous process only and does not apply to the batch process. Vice versa, if the term "process" is used together with "batch", i.e. "batch process", the respective disclosure is related to the batch process only and does not apply to the continuous process.

In principle, any known continuous reactor that is suitable for handling melts can be used in the process according to the invention. Appropriate continuous reactors that can be used for the execution of the process comprises continuous stirred tank reactors, single or twin-screw extruders, single or twin-screw kneaders or combinations of continuous stirred tank reactors, single or twin-screw extruders and single or twin-screw kneaders. Hence the present invention is directed as well to the process that is characterized in that the continuous reactor is a continuous stirred tank reactor, a single or twin-screw extruder, a single or twin-screw kneader or a combination of continuous stirred tank reactors, single or twin-screw extruders and single or twin-screw kneaders.

According to an appropriate embodiment of the invention dimethylammonium chloride and dicyanodiamide are present in the mixture to each other in a molar ratio of from 1.0 to 2.0:1, preferably in a molar ratio of about 1.15:1. Thus, the present invention is also directed to a process, which is characterized in that dimethylammonium chloride and dicyanodiamide are present in the mixture to each other in a molar ratio of from 1.0 to 2.0:1, preferably in a molar ratio of about 1.15:1.

As described above the mixture of dimethylammonium chloride, dicyanodiamide and, if present, metformin HCl as used in step (a) of the process of the present invention contains up to 20% by weight water based on the total weight of dimethylammonium chloride and dicyanodiamide present in the mixture. According to a preferred embodiment water is present in such step in an amount from 0 to 10% by weight, preferably from 0 to 5% by weight, and more preferably in an amount of about 3% by weight, each based on the total weight of dimethylammonium chloride and dicyanodiamide present in the mixture. Thus, the invention is as well directed to a process that is characterized in that the mixture processed in step (a) contains water in an amount from 0 to 10% by weight, preferably from 0 to 5% by weight, and more preferably in an amount of about 3% by weight, each based on the total weight of dimethylammonium chloride and dicyanodiamide present in the mixture.

According to an advantageous embodiment the reaction mixture may contain an additive that increases the reaction selectivity and/or the viscosity of the melted mixture. As used herein the term "reaction selectivity" refers to the ratio of the metformin HCl relative to byproducts obtained in the reaction. When the reaction selectivity is high, the impurity derived from byproducts is reduced or even suppressed. An increased viscosity of the melted mixture is especially advantageous if the process is run as continuous process (e.g. if it is conducted in an extruder or a kneader) as it reduces the flow return against the flow direction. Hence, the invention is also directed to the process that is characterized in that the mixture processed in step (a) further contains an additive that increases the reaction selectivity and/or the viscosity of the melted mixture.

Any solid additive that increases reaction selectivity and/or the viscosity of the melt can be used. Additives that are especially suitable for the process of the invention include sodium chloride, celite or silica or a blend of two or more materials thereof. A preferred additive is celite. Accordingly, the present invention is further directed to the process that is characterized in that the additive is sodium chloride, celite or silica, preferably metformin HCl or celite, or a blend of two or more materials thereof.

In an exemplary embodiment, the additive is present in the mixture in an amount from 0.001 to 50% by weight, preferably from 0.01 to 10% by weight, more preferably from 0.1 to 5% by weight, based on the total weight of dimethylammonium chloride and dicyanodiamide present in the mixture. Therefore, the present invention is also directed to a process that is characterized in that an additive is present in the mixture in an amount from 0.001 to 50% by weight, preferably from 0.01 to 10% by weight, more preferably from 0.1 to 5% by weight, based on the total weight of dimethylammonium chloride and dicyanodiamide present in the mixture.

According to a preferred embodiment of the process, the reaction mixture comprises as additive about 1% celite by weight, based on the total weight of dimethylammonium chloride and dicyanodiamide present in the mixture. Thus, the invention is also directed to the process that is characterized in that the reaction mixture comprises as additive about 1% celite by weight, based on the total weight of dimethylammonium chloride and dicyanodiamide present in the mixture.

Due to the hygroscopic nature of solid dimethylammonium chloride, delivery and handling of this material on large scale tends to be challenging and has the potential to negatively impact process robustness. In order to reduce this risk, dimethylammonium chloride can be supplied as an aqueous solution containing 20 to 50% water by weight, which is concentrated to the required water content before mixing with dicyanodiamide to form the melt mixture.

Accordingly, the present invention is also directed to a process, wherein dimethylammonium chloride is added as a mixture with water, which mixture is prepared by preparing a solution of dimethylammonium chloride containing 20-50% water by weight and concentrating such solution to 0.1 to 20% water by weight, preferably to 0.1 to 10% water by weight, more preferably to about 0.1 to 6% water by weight, each based on the total weight of dimethylammonium chloride and water.

The mixture of dimethylammonium chloride and water can be used in the batch process (the mixture of dimethylammonium chloride and dicyanodiamide is prepared by mixing a mixture of dimethylammonium chloride and water with dicyanodiamide) as well in the continuous process (the dimethylammonium chloride is fed as a mixture of dimethylammonium chloride and water).

The examples, without being restricted thereto, illustrate the invention.

EXAMPLE 1 (BATCH PROCESS, ONE HEATING STEP)

250 g of dicyanodiamide, 315.22 g of dimethylammonium chloride and 16.96 mL of water was added to a 1 L reactor. The reactor is heated to 145° C. for 3 hours. As the reaction proceeds, metformin hydrochloride precipitates from the mixture. The reactor is cooled to room temperature, demineralized water is added to the reactor and the resulting slurry is removed. Metformin HCl is obtained in 89% purity.

EXAMPLE 2 (BATCH PROCESS, TWO HEATING STEPS)

3432 g of dicyanodiamide, 4320 g of dimethylammonium chloride and 232.5 mL of water was added to a reactor. The reactor is heated to 105° C. until a homogeneous melt if formed. The melt mixture is transferred to a 12 L twin screw, co-rotating batch kneader and heated to 130° C. for 1 hour, followed 145° C. for 2.5 hours. As the reaction proceeds, metformin hydrochloride precipitates from the mixture. The reactor is cooled to room temperature, demineralized water is added to the reactor and the resulting slurry is removed. Metformin HCl is obtained in 94% purity.

EXAMPLE 2 (CONTINUOUS PROCESS)

Dicyanodiamide, dimethylammonium chloride in a molar ratio of 1:1.15 and water (3% by weight relating to the total weight of dimethylammonium chloride and dicyanodiamide present in the mixture) was continuously fed to a 6 L stirred vessel heated to 100° C. The melt mixture was transferred at a rate of 4 kg/hr into a stirred reactor, where it is heated to 135° C. for a residence time of 15 mins. The partially reacted material is continuously discharged into a twin-screw kneader, where it is stirred at 175° C. for 45 mins to obtain complete conversion. The product is continuously discharged from the second kneader at a rate of 4 kg/hr via a vertical twin-screw conveyor into a collection flask. The solid mixture collected contains metformin in 89% purity.

EXAMPLE 3 (BATCH PROCESS USING MIXTURE OF DIMETHYLAMMONIUM CHLORIDE AND WATER)

450 g of a 70% aqueous solution of dimethylammonium chloride was added to a reactor equipped with a distilling column. The mixture was concentrated at 130° C. for 2.5 hours until the water content was approximately 5%. To this mixture, 250 g of dicyanodiamide was added. The reactor is heated to 145° C. for 3 hours. As the reaction proceeds, metformin hydrochloride precipitates from the mixture. The reactor is cooled to room temperature, demineralized water is added to the reactor and the resulting slurry is removed.

The invention claimed is:

1. A process comprising preparing metformin HCl by
   (a) continuously feeding dimethylammonium chloride, dicyanodiamide, 0.001 to 50% by weight based on the total weight of dimethylammonium chloride and dicyanodiamide present of an additive that increases the reaction selectivity and/or the viscosity of the melted mixture, which additive is sodium chloride, celite, silica, or a blend of two or more thereof, and optionally water in an amount up to 20% by weight and optionally metformin HCl in an amount up to 50% by weight, each based on the total weight of dimethylammonium chloride and dicyanodiamide present in the mixture, to a reactor under continuous stirring and under continuous heating the mixture to a temperature in the range from 70° C. to 250° C.;
   (b) cooling the reacted mixture and collecting crystalline metformin HCl obtained,
   said process being run in one continuous reactor or in a combination of continuous reactors in series.

2. The process according to claim 1, wherein metformin HCl is present in an amount of 5 to 10% by weight based on the total weight of dimethylammonium chloride and dicyanodiamide present in the mixture.

3. The process according to claim 1, wherein in (a) the mixture is heated to a first temperature in the range from 70° C. to 120° C., which temperature is maintained for a certain time, and then heated in to a second temperature in the range from 120° C. to 250° C., which temperature is maintained for a certain time.

4. The process according to claim 1, wherein the process is run in a combination of continuous reactors in series.

5. The process according to claim 4 run in a combination of continuous reactors in series wherein in (a) the mixture is heated in a first reactor to a first heating temperature in the range from 70° C. to 120° C., which temperature is maintained for a certain time, then heated in a second reactor to a second heating temperature in the range from 110° C. to 160° C., which temperature is maintained for a certain time and then heated in a third reactor to a third temperature in the range from 140° C. to 250° C., which temperature is maintained for a certain time.

6. The process according to claim 5, wherein the sum of all times at which the heating temperature(s) is/are maintained for a certain time ranges from 0.1 minutes to 10 hours.

7. The process according to claim 5, wherein the first heating temperature is maintained for 0.1 min to 2 hours and the second heating temperature is maintained for 0.1 min to 3 hours and the third heating temperature is maintained for 0.1 min to 5 hours.

8. The process according to claim 1, wherein the continuous reactor is a continuous stirred tank reactor, a single or twin-screw extruder, a single or twin-screw kneader or a combination of continuous stirred tank reactors, single or twin-screw extruders and single or twin-screw kneaders.

9. The process according to claim 1, wherein dimethylammonium chloride and dicyanodiamide are present in the mixture to each other in a molar ratio of from 1.0 to 2.0:1.

10. The process according to claim 1, wherein the mixture processed in (a) contains water, in an amount up to 10% by weight, based on the total weight of dimethylammonium chloride and dicyanodiamide present in the mixture.

11. The process according to claim 2, wherein the additive is celite.

12. The process according to claim 10, wherein the mixture comprises as additive about 1% celite by weight, based on the total weight of dimethylammonium chloride and dicyanodiamide present in the mixture.

13. The process according to claim 1, comprising preparing a solution of dimethylammonium chloride containing 20 to 50% water by weight and concentrating such solution to 0.1 to 20% water by weight, based on the total weight of dimethylammonium chloride and water, and feeding the resultant concentrated solution of dimethylammonium chloride in (a).

* * * * *